United States Patent
Jobsis et al.

(10) Patent No.: US 6,594,513 B1
(45) Date of Patent: Jul. 15, 2003

(54) METHOD AND APPARATUS FOR DETERMINING OXYGEN SATURATION OF BLOOD IN BODY ORGANS

(76) Inventors: Paul D. Jobsis, 647 Chestnut St., Dubuque, IA (US) 52001; Frans F. Jobsis, 1834 Bushy Cook Rd., Efland, NC (US) 27243

(*) Notice: Subject to any disclaimer, the term of this patent is extended or adjusted under 35 U.S.C. 154(b) by 0 days.

(21) Appl. No.: 09/481,830

(22) Filed: Jan. 12, 2000

(51) Int. Cl.⁷ .............................................. A61B 5/00
(52) U.S. Cl. ..................... 600/328; 600/323; 600/326
(58) Field of Search ................... 600/309–310, 600/316, 330, 322–326, 336, 328; 356/39–42

(56) References Cited

U.S. PATENT DOCUMENTS

| | | | |
|---|---|---|---|
| 3,923,403 A | 12/1975 | Harklau | 356/201 |
| 4,281,645 A | 8/1981 | Jobsis | |
| 4,510,938 A | 4/1985 | Jobsis et al. | |
| 4,655,225 A * | 4/1987 | Dahne et al. | 356/320 |
| 4,697,593 A | 10/1987 | Evans et al. | |
| 4,805,623 A | 2/1989 | Jobsis | |
| 4,908,762 A * | 3/1990 | Suzuki et al. | 600/407 |
| 4,997,769 A | 3/1991 | Lundsgaard | 436/66 |
| 5,249,584 A * | 10/1993 | Karkar et al. | 600/578 |
| 5,253,646 A * | 10/1993 | Delpy et al. | 600/310 |
| 5,337,745 A | 8/1994 | Benaron | |
| 5,377,674 A | 1/1995 | Kuenstner | |
| 5,413,100 A * | 5/1995 | Barthelemy et al. | 600/328 |
| 5,692,503 A | 12/1997 | Kuenstner | |
| 5,722,398 A * | 3/1998 | Ishihara et al. | 600/322 |
| 5,782,756 A * | 7/1998 | Mannheimer | 600/322 |
| 6,049,727 A * | 4/2000 | Crothall | 600/310 |
| 6,195,574 B1 * | 2/2001 | Kumar et al. | 600/323 |

OTHER PUBLICATIONS

Journal of Applied Physiology vol. 43, pp. 858–872, article by Jobsis, Kezer, LaMana and Rosenthal.

* cited by examiner

*Primary Examiner*—Eric F. Winakur
*Assistant Examiner*—Matthew Kremer
(74) *Attorney, Agent, or Firm*—Olive & Olive, P.A.

(57) ABSTRACT

A spectrophotometric method and apparatus for determining the degree of oxygen saturation of the hemoglobin in the blood within a body part utilizes differences in light absorption based on differences in extinction coefficients at different wavelengths. Oxygen saturation is determined by utilizing absorption at three or more wavelengths of radiation preferably in the near red and infrared region (NIR) of the spectrum, specifically tailored to two or more components to be detected by the radiation. The first (reference) wavelength is preferably chosen to be at an isosbestic point for the two components, commonly the oxygenated and deoxygenated forms of hemoglobin. The absorption at the isosbestic point is subtracted from the absorption at the other wavelengths. Using these differences in absorption, the amount of each of the components encountered by the light may be determined without determination of pathlength, which would be required to determine the concentration. In order to determine the oxygenation state, i.e. ratio of oxygenated to deoxygentaed blood components, knowledge of the relative amounts suffices. Interference from other light-absorbing components, specifically those that respond to the oxygenation state of the body part (such as cytochrome c oxidase) is in the three wavelength method eliminated by reiterative correction.

16 Claims, 3 Drawing Sheets

METHOD AND APPARATUS FOR DETERMINING OXYGEN SATURATION OF BLOOD IN BODY ORGANS

BACKGROUND OF THE INVENTION

1. Field of the Invention

This invention relates to spectrophotometric methods and apparatus for quantitatively determining the degree of oxygen saturation of the hemoglobin in the blood within a body part or organ, and in particular pertains to determination of the percent oxygen saturation of intra-cerebral blood.

2. Description of the Related Art

Background

It is generally known that metabolism and more particularly oxygen sufficiency and adequacy of utilization are parameters of fundamental importance in assessing the function of any body organ. This is made self-evident when one considers that the energy provision for tissue function is underwritten for better than 90 percent by oxidative reactions involving the reduction of $O_2$ to $H_2O$. In the absence of sufficient oxygen, this process becomes impaired with a corresponding impairment in organ function. Also recognized is the fact that an excess of oxygen also impairs organ function. For ease of explanation, the description to follow is based primarily on considering the effect of an insufficiency rather than an excess of oxygen.

In instances of extensive oxygen deprivation, over a period of time the organ loses viability and as a result the individual often has the same fate, especially if that organ is the brain. Although all organs are adversely affected by oxygen insufficiency, perhaps the problem is most acute in the case of the brain because of its complete dependence on oxidative metabolism for proper function and viability. For example, an absence of oxygen in the brain for more than a dozen seconds produces dysfunction and an absence for longer than a few minutes spells irreversible damage. A less acute impairment of oxygen availability leads to a gradual loss in brain function, especially with respect to the higher centers of the cerebral cortex. An excess of oxygen will also adversely affect the brain. For example, a neo-natal patient may well go blind by reason of excess oxygen.

Because of the vital role that oxygen sufficiency plays in human physiology, intensive efforts have been made over the years to measure this parameter in various organs and most particularly in connection with the assessment of brain and heart function. Numerous spectrophotometric methods exist for non-invasive, continuous, monitoring of metabolism in a body organ both by use of transillumination and reflectance. By "transillumination" is meant the practice of passing light through a body organ and by "reflectance" is meant the practice of diffusely reflecting light from a body organ. These methods are used primarily as instruments to determine the fraction of total hemoglobin in blood that carries oxygen. By common agreement, oxygenated hemoglobin is designated $HbO_2$ whereas Hb refers to the deoxygenated form and total hemoglobin is abbreviated $Hb_t$.

For about half a century, physicians have relied on measurements of the percentage of the hemoglobin in the blood that is saturated with oxygen (the "% $O_2$ Sat") in attempts to assess the oxygenation of tissues. The introduction of this parameter, measured in blood samples drawn from the patient, was a great step forward over the visual observation of the color of various tissues (skin, gums, fingernail beds, etc.)

By common practice, arterial blood samples are used for the assessment of the % $O_2$ Sat. Venous blood samples vary unpredictably depending on the metabolic activity of the organ(s) drained by the donor vein. Even in a given organ blood can be channeled through bypass vessels that can and do vary in their dilation or constriction thus changing the fractions of the blood in the nutritive and in the bypass circulations. Mixed central venous blood as taken from the right side of the heart is difficult to obtain and is therefore not routinely available. It also lacks the specificity required for the assessment of oxygenation status of individual organs.

Although arterial blood has the identical % $O_2$ Sat throughout the body, the parameter does not predict adequacy of organ oxygenation. Matters are complicated by such unknowns as the rate of blood flow, the pH and the $CO_2$ content and by the amount of hemoglobin in the blood which affects the total amount of $O_2$ that can be transported. Instrumentation has been devised to measure these complicating factors in the blood samples and the use of radioactive molecules has been introduced to measure blood flow in certain organs, especially the brain.

In addition for the spectrophotometric measurements of blood in intact tissues, it should be recognized that, depending on the oxygen supply, the oxidative metabolic enzyme cytochrome c oxidase has an absorption spectrum in the spectral region used (750–950 nm). Corrections for this problem have not been introduced in the present art.

Starting in the 1930's, many attempts were made to determine oxygenation status non-invasively by optical means, i.e. to substitute instrumentation for the physicians eye. None of these instruments was truly successful or affordable in the routine clinical setting until introduction of the so-called pulse oximeter in the early 1980's which provides arterial % $O_2$ Sat values in a non-invasive manner. The technique depends on measuring the color of new blood entering the field of observation with each heartbeat. Typically the finger tip, earlobe or toe is transilluminated with two wavelengths, one in the visible (VIS) and one in the near infrared (NIR) range of the spectrum. Alternatively, reflectance optics may be used as described in U.S. Pat. No. 5.692,503. The stable background light signal is subtracted from the measurement made during the pulse of new blood arriving after the heartbeat. Several U.S. patents teach the pulsatile approach by either transillumination or reflectance (see for example U.S. Pat. No. 5,337,745) for either hemoglobin determinations or concentrations of other blood components such as glucose. Thus this oxygenation measurement again reports on the % $O_2$ Sat (or on concentrations of other components) in the arterial blood. The measurement therefore reports only on the quality of pulmonary function in oxygenating the blood. No information is present about oxygen sufficiency in the tissue(s).

With pulse oximetry, all the drawbacks and limitations of the arterial sampling techniques are still present and in fact are exacerbated by the absence of a sample in which hemoglobin and $CO_2$ content and the pH can be measured. Also, the technique requires firm pulsatile flow which is often not present in seriously ill patients and is frequently not measurable in deeper tissue such as the brain.

It can thus be seen that the field of physiological monitoring of patient oxygenation status requires a fundamentally different approach that provides information on the steady state of tissue oxygenation rather than being limited to the efficacy of pulmonary function.

A further aspect of the prior art to be appreciated is the application of the so-called Beer-Lambert law for determining concentrations of light absorbing molecules by measuring circuit parameters from two conditions, for instance of the light being transmitted in the absence of these molecules and in their presence or alternatively the light intensity measured directly without passing through the test subject as compared to the light being transmitted through the test subject. Various literature sources discuss how this law is applied, one such source being U.S. Pat. No. 3,923,403 and another being the above-mentioned U.S. Pat. No. 5.692,503.

An appreciation of how various combinations of measuring and reference wavelengths have been applied in the prior art for physiological measurements is also deemed useful to an appreciation of the present invention. Typically a single "reference" wavelength is used for samples that have a tendency to scatter light. The data from a measuring wavelength is then compared to those from the reference. The former is commonly chosen to be that of the absorption peak whereas the reference is chosen at a more neutral wavelength. The use of two reference wavelengths straddling the measuring one is advocated in U.S. Pat. Nos. 5,377,674 and 5,692,503 and is shown in an article by Jöbsis, Keizer, LaMana and Rosenthal published in 1977 in the *Journal of Applied Physiology*, Volume 43, pages 858 to 872. U.S. Pat. Nos. 4,281,645; 4,697,593; 4,997,769; 4,805,623; and 5,337,745; may be referred to for additional background examples of various singular and multiple wavelength combinations, some of which reside within the near infrared region of interest to the present invention. While the prior art thus does provide means for extra and/or intra-corporeal detection and measuring of blood oxygenation, it can be noted with reference to all such prior art that none of the methods or apparatus of the prior art provide apparatus and methods for intra-corporeal, in vivo, in situ, detecting and measuring the degree of oxygenation of the hemoglobin in the blood within a tissue or organ in the manner of the present invention and independent of the path length. The disclosure of the foregoing and all other patents and publications referred to herein are incorporated herein by reference.

Prior Art Practices Specifically Related To Measuring Oxygen Saturation In Tissue Analyzing tissue oxygenation by hemoglobin oxygen saturation requires choosing the wavelength range to be utilized and accurate measurement of in vivo spectra of oxygenated and deoxygenated tissue in that range. In this regard, a part of the near infrared (NIR) region (i.e. 700 nm to 950 nm) is favored over the better known visible range (450 to 700nm) because of the muted light scattering properties of the longer wavelengths. Nevertheless, measurements are also possible in the extended range of 600 to 1300 nm as disclosed below. In addition, only three oxygen sensitive molecules (hemoglobin, Hb; myoglobin, Mb; and cytochrome c oxidase previously known as cytochrome $aa_3$ and abbreviated cyt c ox), absorb light of these wavelengths. Hemoglobin and myoglobin have practically identical NIR absorption spectra, both in their oxygenated ($HbO_2$ and $MbO_2$) and de-oxygenated (Hb and Mb) forms. Thus, the NIR measurements are of $HbO_2+MbO_2$ and of Hb+Mb respectively. During cerebral monitoring the myoglobin contribution is trivial to absent since it only occurs in muscle cells. However, when monitoring muscle tissue, the Mb and $MbO_2$ contributions are significant. In cerebral measurements the cyt c ox contribution to the total optical signal can vary and under certain pathological circumstances may be sufficiently large to produce a substantial error in the hemoglobin determinations.

Non-invasive determination of the concentration of blood components Hb and $HbO_2$ in intact biological tissues and body organs utilizing spectrophotometry is complicated by the fact that these measurements are made in a turbid, optically impure, multiple-component environment. In such an environment, particularly in body tissues and organs, light scattering, even at NIR wavelengths, generally results in greater, sometimes much greater, loss of light than is lost by actual absorption of the incident light by the various light absorbing molecular species present. In addition, scattering increases the path the photons travel from the input point to the point of collection. This defeats use of the Beer-Lambert law which requires exact knowledge of the optical path length.

The in vivo spectra differ from the in vitro spectra of purified hemoglobin due to light scattering by the tissue, which is not the same at all wavelengths, not even in the NIR. The shorter the wavelength, the more intense light scattering becomes. This has two consequences: photons at shorter wavelengths are more easily lost by being scattered away from the detector and, photons of shorter wavelength that finally do reach the detector have traversed a longer path than the longer wavelength photons since the former are scattered more frequently. This results in a greater degree of absorption of lower wave-length photons and thus to a skewing of the absorption spectrum. Various means— physical, chemical and computational - have been introduced to overcome problems such as those described. Such problems are greatly exacerbated however when an attempt is made to measure the $O_2$ saturation of the blood within large organs (the brain, the heart, etc.) rather than small thin ones such as ear lobes, finger tips, and the like.

Review Of Method For Quantitative Analysis By Spectrophotomety

The Beer-Lambert law equation defines the relationship between light absorption, absorber (solute) concentration, extinction co-efficient and optical path length as follows:

$$\log I_o/I = d \cdot e \cdot \text{concentration, where:}$$

Io is the intensity of the light transmitted through the medium (solvent) in the absence of the absorber to be measured;

I is the intensity of transmitted light in the presence of the absorber;

Log $I_o/I$ is variously called the Absorbance, Absorbancy or Optical Density;

d is the length of the optical path through the sample;

e is the molar (or milli-molar or micro-molar) extinction co-efficient, i.e. the light loss incurred (the absorption measured) during passage through a one molar (a milli or a micro-molar) solution over 1 cm; dimension: moles×liter$^{-1}$×cm$^{-1}$).

Once the optical density is determined of a solution of a single, known absorber with known e in a vessel of known pathlength, the concentration of that solute can be calculated.

Traditionally, extinction coefficients are determined by analyzing the light losses when beams of mono-chromatic light are transmitted through a vessel (cuvette) of known path length containing a clear (non-opalescent, non-scattering) solution of known concentration. At different wavelengths the extinction coefficients will vary; a graphic representation of these coefficients on a wavelength scale is called the absorption spectrum of the absorbing compound.

In nature clear, non-scattering solutions are rare exceptions. Spectrophotometry of natural entities must therefore cope with substantial light scattering of incident light. This causes distinct problems as previously referred to: (a) light is not only lost by absorption but also by being scattered away from its path to the detector; and (b) light that does reach the detector will have traveled a random, helter-skelter route of unknown path length as it is scattered multiple times before emanating from the object. This is an especially serious limitation for large, dense objects, from which only a dim light can be perceived, as is the case for the human head and brain.

The degree of light scattering and therefore the optical path elongation is due to a complex combination of the wavelength, the geometric length of the optical path, the shape and size of the scattering particles and the difference in the indices of refraction between the solvent and the particles, which in biological samples are more glazy than specularly reflective. In addition, this difference varies with the metabolic state because of shifts of ions and water in the cells. Thus, it is not possible to construct a comprehensive mathematical expression to correct with sufficient precision for the differences between the geometric and actual optical path length traversed in vivo.

Previous oxygen saturation determination methods in body parts generally required measurements through only thin body parts such as the ear lobe or the finger tip in which multiple scattering is sufficiently small so as not to affect significantly the absorption spectra of hemoglobin and the observed concentrations of Hb and $HbO_2$. In significant contrast, determining the actual path length traveled by the radiation through a longer body part requires complex and expensive biophysical instrumentation and difficult experimentation. In the case of human infant's heads, the results have been found to be about 3–6 times greater than the path length determined by simply measuring the width of the body part between the points of illumination and detection, i.e. the geometric path length. Therefore, determining the actual path length taken by the radiation through a relatively long body part, is complicated and subject to error and unreliable when trying to determine the oxygen saturation of the blood. In the application of optical monitoring to larger solid organs, it is possible to utilize the back scattering of light out of the tissue by so-called diffuse reflectance. In this case, the input and detection points are several centimeters apart on the same surface of the solid organ, as was described earlier in U.S. Pat. 4,281,645.

From the foregoing description and other description to follow, the shortcomings in the prior art methods and apparatus for determining oxygen saturation of the hemoglobin in the blood within a body organ can be characterized as follows:

(a) they require determination of actual concentrations of Hb and $HbO_2$;
(b) use of the Beer-Lambert law is defeated since use of this law requires exact knowledge of the optical path length;
(c) as the invention recognizes, path length correction factors are quite variable, should be determined from case to case and should be continuously updated for changes in metabolism, but neither is possible with the prior art;
(d) the variable degree of absorption by cytochrome c oxidase is not corrected for;
(e) as the invention further recognizes, light scattering introduces significant deviations from standard extinction coefficients; deviations that differ depending on wavelength but in the prior art no accounting is made for this skewing of the absorption spectra;
(f) no means or method is provided for distinguishing scattering losses from absorption losses;
(g) differences in optical path length created by large differences in measuring wavelengths and therefore in wavelength dependent scattering are not corrected for;
(h) previous apparatus, especially those for pulse oximetry, used to determine % $O_2$ Sat of arterial blood lack means or method for mitigating effects of distortion by scattering;
(i) no provision is made for entering the light of various wavelengths homogeneously into the body organ at a single point of entry;
(j) the adequacy of organ oxygenation is not revealed since the cyt c ox is not monitored and therefore not corrected for; and
(k) firm pulsatile flow is required.

Objects of Invention

It is therefore an object of this invention to provide a method and apparatus for determination of the degree of oxygen saturation of the hemoglobin in the blood within tissues and organs (the "% Tissue Blood $O_2$ Sat") such as the head or other organ or body parts, such as the heart or muscle tissue which minimizes the error due to the scattering of light.

It is another object of this invention to eliminate the error contributed by cytochrome c oxidase.

It is a further object of this invention to provide a method and apparatus for determination of the described degree of oxygen saturation in which knowledge of the optical path length and concentrations of Hb and $HbO_2$ are not needed.

It is another object of this invention to provide a method and apparatus for determination of the described degree of oxygen saturation in which the skewing of absorption spectra has been accounted for.

It is a further object of this invention to provide a method and apparatus for determination of the described degree of oxygen saturation in which the effect of scattering and scattering changes is minimized.

It is also an object of this invention to provide a method and apparatus which permit in situ extinction coefficients to be utilized in making a determination of the degree of oxygen saturation of the hemoglobin in the blood within a body organ tissue.

It is a further object of the invention to furnish a device by which the presented wavelengths are homogeneously entered into the body part or organ at the same point.

It is also an object of this invention to eliminate the necessity to assign pathlength correction factors by which the geometrical distance between input and receiver should be multiplied to approximate the optical pathlength.

Other objects and advantages will be more fully apparent from the following disclosure and appended claims.

SUMMARY OF THE INVENTION

In general, the shortcomings of the prior art systems and methods for determining the degree of oxygen saturation of the hemoglobin in the blood within a body organ are overcome, circumvented or mitigated by the system and method of the invention which are characterized by the following important features:

1. The method of the invention causes subtraction of the absorption signal at the $Hb/HbO_2$ isosbestic wavelength (see definition below) from the absorption signals at the other wavelengths; the differences are then utilized to create multiple simultaneous equations which can be solved for the multiple absorbing components;
2. In the case of unavailability of a laser at the isosbestic wavelength, the method and apparatus of the invention permits use of two or more lasers producing wavelengths of light near the isosbestic one, preferably straddling the isosbestic one.
3. In the method and apparatus of the invention, there is a realization of the ability to deduce oxygen saturation of the blood in the tissue without determining the concentrations of the two forms of the hemoglobin;
4. The invention method provides correction for or solution of the redox state of cyt c ox;
5. The apparatus and method of the invention obviates the need to determine scattering or scattering changes to prevent errors by changes in metabolism during the monitoring period;
6. The method of the invention requires at least three wavelengths - one isosbestic and two measuring ones—while permitting addition of a fourth (or more) measuring wavelengths to simplify application of the invention or cope with limitations in availability of lasers with preferred wavelength output; and
7. The method and apparatus of the invention also prevents errors caused by local arterial and venous blood vessels through use of a light mixer or homogenizer with a single aperture to enter light into the body.

More specifically, the method and apparatus of the invention provide means for intra-corporeal, in-vivo, in-situ, detecting and measuring the degree of hemoglobin oxygenation in tissue independent of the optical path length. The method and apparatus of the invention ascertains the clinically important physiological parameter "% TissueO$_2$Sat" (i.e. percent of hemoglobin in the blood within tissues in a body part that is oxygenated). In this regard the method and apparatus of the invention determines the ratio of HbO$_2$ to (HbO$_2$+Hb) without the need for determining the actual concentrations of Hb and HbO$_2$.

Where the term "body part" is used in the description and is later used in the claims in reference to the invention, it will be understood that such term is meant to refer to a part of a human, animal or other living body exhibiting active oxidative metabolism. For example, with respect to a human body, such "part" might, for example, be the hand, heart, head, kidney, liver or tumor of an individual being tested for percent oxygen saturation of the hemoglobin in the blood within such part. The heart, head, kidney and liver by way of example are each also typically recognized as being an "organ" as such term is used in the description. The term "tissue" is also used in the description to refer to a component of such body part or organ.

In its preferred embodiment, the present invention utilizes a single reference wavelength and two or more measuring wavelengths. The strength of the received signal of the reference wavelength radiation is subtracted from those of the two or more measuring wavelengths.

The method and apparatus of the invention, unlike the practices of the prior art, introduces a means to assess accurately the degree of oxygenation of the blood within an organ notwithstanding the unknown pathlength elongation and increases the reliability of the measurements by correcting for the skewing of absorption spectra and for variable absorbance contributions of cytochrome c oxidase.

In the preferred embodiment of the invention, light at multiple wavelengths, typically three, four or more different wavelengths, is defocussed and preferably mixed before being entered into the body organ or tissue at exactly the same location on that organ. The absorption at the isosbestic (reference) wavelength of the oxyhemoglobin and deoxyhemoglobin components, (i.e. where the absorption is the same for the two forms of the molecule) is subtracted from the absorption at two or more other (measuring) wavelengths. Thus, the first (reference) wavelength is preferably chosen to be at or near (within about 10 nm) the isosbestic point for the two components (Hb and HbO$_2$), which is about 815 nm (between 810–820 nm). In the three wavelength technique, the two other wavelengths are preferably in the 780 nm and 900 nm regions. When three measuring wavelengths are used, they are preferably in the ranges of 750–785, 860–875 and 895–915 nm, respectively. Visible wavelengths in the red region of the visible spectrum (600 to 700 nm) and the farther NIR region of 1100 to 1300 nm can also be employed.

The total light loss at the reference wavelength (i.e. by scattering and by its absorption by tissue components, fib and HbO$_2$ primarily) is subtracted from the total light loss at each of the other wavelengths. The subtraction removes the effect of scattering, assuming scattering across the NIR range of interest (750 nm to 950 nm) is nearly constant per wavelength difference. As later explained, the residual effect that scattering has on the skewing of the absorption spectra of hemoglobin and cyt c ox is corrected for by using their in vivo, in situ spectra rather than their in vitro spectra.

Using the differences between the detected electronic signals of the different wavelengths rather than the total signals (scattering loss plus absorption loss), the amount of each of the two components, i.e. Hb and HbO$_2$, may be determined. Subsequently the ratio of the amounts is used to obtain a dimensionless number corresponding to oxygen saturation in terms of % Tissue Blood Oxygen Saturation, i.e. for cerebral tissue % CBOS. Thus, the concentration of Hb and HbO$_2$ do not need to be determined. This circumvents the need to determine the optical pathlength in the tissue and avoids further errors when this pathlength changes.

The apparatus of the invention provides a source of multiple wavelengths, a device for mixing the wavelengths, received directly from the sources, prior to entering the light into the body organ, means for directing the mixed wavelengths at a single point of entry, a detector for measuring the input intensity of each wavelength and one for measuring its intensity after its attenuation by the tissue and a processor for processing signals related to the absorption to produce the number referred to above (% Tissue Blood O$_2$ Sat) according to the method of the invention.

DETAILED DESCRIPTION OF THE INVENTION AND PREFERRED EMBODIMENTS THEREOF

Summary Of Problems Recognized And Dealt With By Invention

In contradistinction to the methods set forth in recent U.S. Pat. Nos. 5,377,674 and 5,692,503, the disclosures of which are incorporated by reference, the method of the present invention does not depend on pulse oximetry (which requires the detection of pulsatile flow in the body part) nor on sufficiently small in vitro samples or in situ body parts to avoid major distortions of the absorption spectra. Nor does the present invention use "derivative spectrophotometry" in the NIR, as specified in the two patents referenced above, to calculate the concentrations of Hb and $HbO_2$ and thus determine the % $O_2$ Sat.

Figures 5, 6:
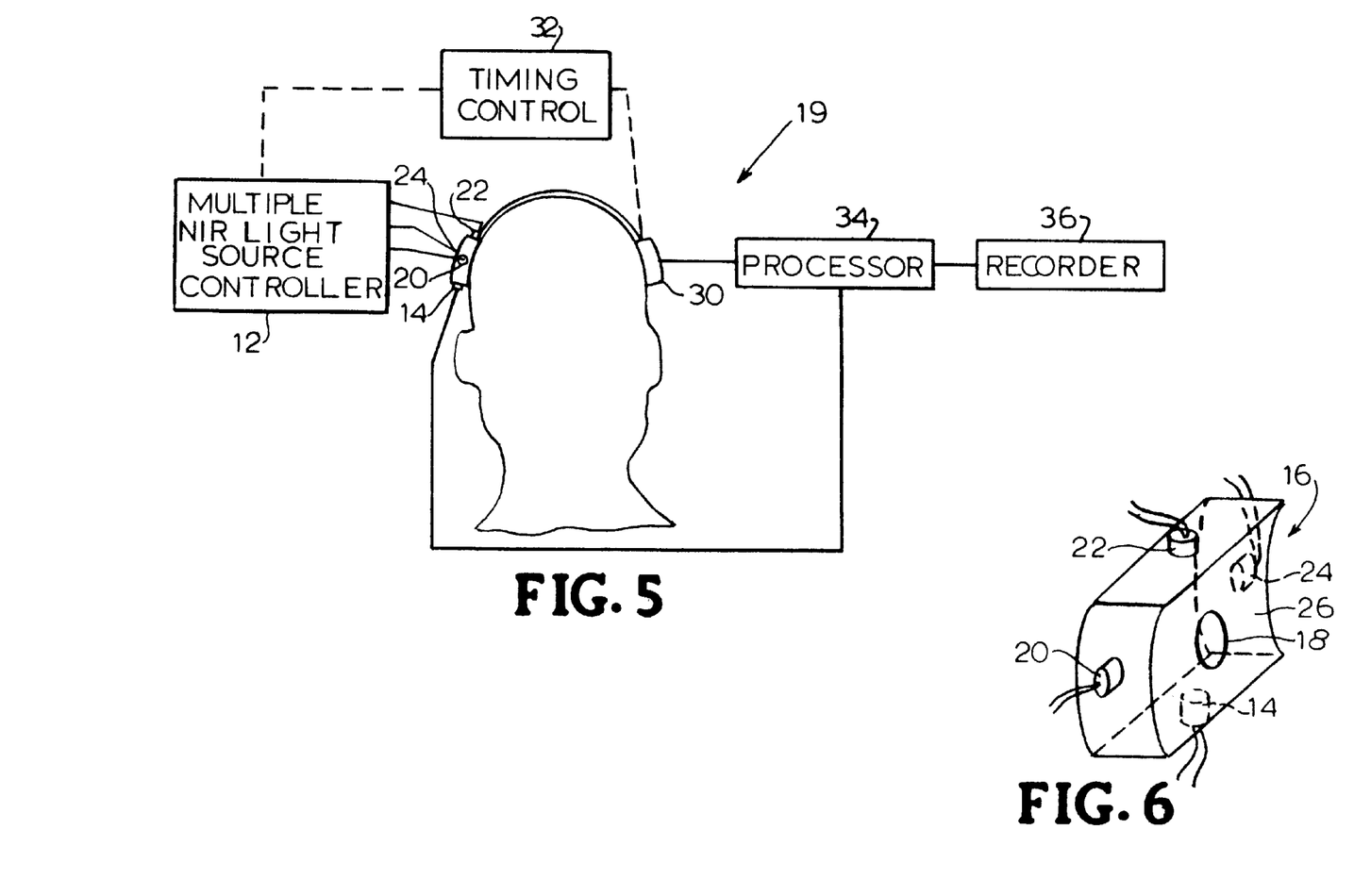
FIG. 5 is a schematic drawing of a system incorporating the invention.
FIG. 6 is a perspective view of a homogenizer or mixer component used in the invention system of FIG. 5.

While the standard oxygenation parameter determined in blood samples is commonly abbreviated % $O_2$ Sat., in the case of measurements of blood within the tissue, we use the terminology "% Tissue $O_2$ Sat". or more specifically "% Tissue-Blood $O_2$ Saturation". Since our measurements on the brain are confined to the region between the optical input and detection points as shown in FIG. 5, we use "r CBOS" for "regional Cerebral Blood Oxygen Saturation".

The present invention is designed to monitor deeper tissue such as the brain and also compensates for the absorption by cytochrome c oxidase, an enzyme prevalent in tissues with active oxidative metabolism (such as the brain, the heart, etc.) but practically absent in blood and in peripheral body parts (finger tip, ear lobe, skin, etc.) in which blood flow primarily performs a role in temperature maintenance. In addition, the present invention expressly avoids the combination of widely separated wavelengths, such as combining those in the visible (VIS) with those in the near infrared (NIR) ranges which would maximize differences in optical pathlength created by the differences in wavelength-dependent scattering. The invention recognizes that optical pathlength differences would not only lead to the sampling of different regions by the VIS and NIR radiation, but VIS light would not penetrate scalp and skull sufficiently to produce a viable signal.

The scattering effect is recognized as having the advantage that it generates so-called diffuse reflection, i.e. photons are scattered back from inside the organ and in a diffuse rather than a specular, mirror-like manner. The invention recognizes that the scattering effect can be used to sample, by input and detection at the same surface, the more superficial layers of tissue in large objects, such as the adult human head, which produce too much attenuation for a useful signal in a transillumination mode. With appropriate distance of input and detection the deeper, cerebral cortex can be accessed and emphasized over the superficial scalp and bone. In both the transillumination and reflection techniques, however, the present invention recognizes in conjunction with recognizing the previously stated shortcomings in the prior art methods and apparatus that at least seven major problems exist that are relevant to the attempt to obtain a quantitative assessment of tissue blood oxygenation, in light scattering tissues and organs. These are: 1) the need for distinguishing scattering losses from absorption losses, 2) the presence of differences and changes in scattering intensity at various wavelengths, 3) unknown length of the optical path; 4) the tendency of the optical path length to change with changes in metabolic status; 5) the lack of means to detect and correct for changes in path length in the tissue or organ being examined; 6) the presence of multiple absorbing components, i.e. the occurrence of various light-absorbing molecular species, and 7) the need for having to deal with differences in in vivo absorption coefficients at various wavelengths compared to the standard values obtained from clear solutions in vitro. The enumerated problems are next discussed in the same numerical sequence and the response of the invention method and apparatus to the problems is later discussed in more detail.

1 and 2) light scattering denies the photons a straight path through a solid tissue or organ. After a small fraction of a centimeter, a beam of visible (VIS) range light has not only lost almost all collimation of the beam but has suffered severe attenuation. Light of the near infrared region (NIR) is scattered less intensely but suffers loss of almost all collimation in a centimeter or so, depending on the tissue. Such losses of photons by scattering away from the intended detector are indistinguishable from absorption losses by biochemical components in the tissue. The invention recognizes that only the latter is the means by which the concentration of these absorbing molecules can be assessed by the Beer-Lambert law equation.

3, 4 & 5) To aggravate the situation, the extent of optical pathlength elongation is not only unknown but can and usually does change with changes in metabolic status especially as the tissue approaches a critical decrease in energy status due to a severe dearth of oxygen, i.e. due to severe hypoxia. Recognized by the invention is the fact that this is caused by shifts in the intracellular water content when the ionic pumps fail. This is not a trivial hindrance to satisfactory optical monitoring of oxygen sufficiencies since it is exactly this life-threatening situation that calls for accurate information to guide treatment.

6) As noted before, few biochemical tissue components absorb in the NIR region. Fewer yet change absorption intensity depending on the presence of $O_2$. Of these, Hb and $HbO_2$ (as well as Mb & $MbO_2$) are the strongest absorbers. Cyt c ox does however absorb sufficiently strongly in the hemoglobin isosbestic region (810–820nm) to affect the Hb/$HbO_2$ determinations.

7) The relative absorption strengths at specific wavelengths is unpredictably distorted by the above noted scattering effects. The invention mitigates these effects by using the in vivo and/or in situ absorption spectra generated directly from examples of the organ to be monitored or closely similar ones.

General Description Of Features Of Invention

As an overview prior to describing the details of the invention, it may be noted that the present invention provides a method and apparatus for ascertaining the clinically important physiological parameter "%Tissue $O_2$ Sat" (i.e. percent of hemoglobin in the blood within the tissue that is saturated with oxygen). The invention determines the ratio of $HbO_2$ to ($HbO_2$+Hb) without the need for determining the actual concentrations of Hb and $HbO_2$. Essentially and importantly, the aforementioned "blood" is the entirety of the hemoglobin contained in all three major compartments, i.e. arterial, capillary and venous, in the tissue being monitored.

This approach is taken in contra-distinction of the commonly used % $O_2$ Sat of the arterial blood alone measured with the so-called pulse oximeter and also of methods requiring determination of the concentrations of the absorbing components. As later explained, if the relative tissue absorptions are known at a minimum of three wavelengths, one being hemoglobin's isosbestic point, the method and apparatus of the invention through their unique approach in dealing with the mentioned problems permits one to calculate the oxygen saturation of the blood in the tissue.

Also to be noted is that the present invention provides: 1) an apparatus for presenting known amounts of harmless Near Infrared (NIR) "light", made up of a sequence or mix of several wavelengths within the NIR range, to the exterior surface of a body organ or to the skin and/or bone covering it, i.e. such as scalp and skull, and for measuring the intensity of that light emanating from that organ at a distant point; and 2) a method of determination of oxygen saturation of the blood continuously, in situ, in vivo by utilization of NIR irradiation, for the determination of oxygen saturation of hemoglobin in the local blood vessels. (As previously mentioned and as used herein, the designation "Hb" refers to deoxygenated hemoglobin whereas oxygenated hemoglobin is referred to as "$HbO_2$" or "HbO" interchangeably.)

To increase the accuracy of the cyt $aa_3$ determination and therefore of the cerebral blood oxygenation, the initial calculation of the tissue oxygenation, if significantly different from normoxia (e.g. 60–75% oxygenation, instead of normoxia at 50–55%), is used only as a first estimate of the redox state of cyt c ox. The actual absorbance correction in the tissue oxygen equation is then re-calculated using the previous determination in a reiterative process as discussed herein. In other words, from existing knowledge of the relation between the blood oxygen saturation and the cyt $aa_3$ redox state (FIG. 3), the first determination of oxygen saturation enables us to estimate the cyt $aa_3$ redox state. This determination allows us, in turn, to better refine the determination of the oxygen saturation which leads to a better $cytaa_3$ redox state estimate and so on, repeatedly until sufficient accuracy has been reached. The regional cerebral blood oxygen saturation as thus finally determined is termed the regional Cerebral Blood Oxygen Saturation or "r CBOS."

Figure 3:
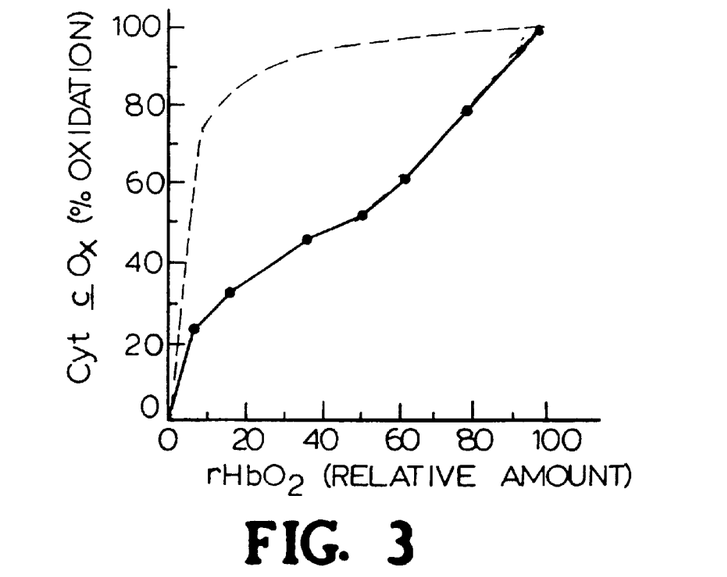
FIG. 3 shows a plot (solid line) of the interrelation, observed by the inventors, between the amount of intracerebral HbO$_2$ and of oxidized cyt c ox in the brain of an anesthetized cat being ventilated with various gas mixtures from 95% O$_2$+5% CO$_2$ (top right data point) to 100% N$_2$ (bottom left). The broken line represents the (hypothetical) interrelation in another (hypothetical) tissue in which cyt c ox reacts differently to the same regimen of ventilatory gas mixtures.

When determining the oxygen saturation of a body part (for example, a person's head) one can start with the assumption of a normoxic oxidation state of cytochrome c oxidase and hemoglobin of 50% for the initial determination of oxygen saturation (FIG. 3). If, however, the oxygenation at the first calculation is 30%, not 50%, then the cyt $aa_3$ oxidation state should have been lower also, say 40% as is found in the look-up table incorporated in the instruments program. However, the absorption by cyt $aa_3$ at 40% rather than 50% is known to affect the light absorption at several of the Hb and $HbO_2$ determining wavelengths. The mathematical routine will now recalculate the blood saturation and find it to be say 37%, at which level however the contribution of oxidized cyt $aa_3$ would be slightly higher and must be recalculated. More accuracy in the resultant determination of the oxygen saturation can be gained by repeating such reiterative determinations.

The apparatus and method are next generally described and are later described in reference to the drawings.
Detailed Description Of Invention Apparatus And Method A preferred apparatus 19 (FIGS. 5 and 6) is described that controls and measures the NIR light and mathematically processes the signals. A unique device, the "mixer" 16, mixes the light from multiple lasers with different wavelengths in order to enter it homogeneously into the scalp from a single aperture 18. It also carries detector means 14 to measure the intensity of the light at each wavelength. The mixer 16 is preferably relatively flat and has a flexible housing which is lined internally with a NIR reflective material, such as aluminum film, filled with a clear material, such as a stiff silicone gel, containing white, ( i.e. non-absorbing and wavelength independent) scattering particles, such as titanium dioxide powder, which disperses the light entering the mixer. Housing 26 may be formed of a strong but somewhat pliable plastic such as found for example in the walls of plastic containers for oil and the like or squeezable containers such as modern plastic toothpaste tubes. The aperture 18 of the mixer 16 is pressed against the skin after application of a thin layer of silicone coupling gel to eliminate any air which would diminish transmission of light by differences in the index of refraction between gel-air-skin interfaces.

The "light" of three or more lasers 20, 22, 24 mounted on the edges of housing 26 and producing NIR radiation at distinct wavelengths is entered into the mixer 16 by having the lasers mounted directly on the housing 26 of mixer 16. Aside from this preferred device embodiment, mounting the lasers and mixer directly on a head band, not shown, such as described in Patent 4,510,938 can also be effective. Recognizing that the input detector measures intensity of each laser input, the light can be presented sequentially or is truly mixed when all three lasers are on at the same time (say, when using a modulation technique), but it is always decollimated and entered in the body organ at a single location.

The small solid state incoming light detector 14 is mounted on the mixer 16 to measure the intensity of the light within it. This signal can be used as an equivalent to the $I_o$ of the Beer-Lambert law equation, the light intensity signal before absorption or scattering losses in the tissue.

A solid state detector 30 having a surface area larger than that of detector 14 is applied to the skin either diametrically opposite the entry point for transillumination measurements of small body parts such as a newborn's head, or several cm away on the same aspect of the body part for diffuse reflectance application when measuring larger organs such as the adult head. It is important that the two detectors 14 and 30 have the same spectral response to NIR radiation and that the two signal treatment paths in the processor are identical, except for an adjustable gain to approximately equalize the two signals for each wavelength. The apparatus 19 of the invention includes a timing control 32, a processor 34, and a recorder 36 connected in the manner of FIG. 5. The function of these components will be well understood by reference to the prior art cited above and the description of the invention to follow.

The method of the invention and apparatus provided by the invention pertains to the treatment and processing of the "raw" optical signals to obtain the %$TissueO_2Sat$ signals in the presence of large scattering losses.

The invention recognizes that oxygen saturation of the blood in a region can be expressed as a percentage equal to:

$$\% \text{ TissueBloodO}_2\text{Sat} = \frac{\text{Amount of HbO}_2}{\text{Amount of HbO}_2 + \text{Amount of Hb}} \times 100$$

Each of the terms in the above expression designating an "amount" is effectively directly related to the number of $HbO_2$ or Hb molecules that absorb photons while they travel through the tissue, rather than the concentration of these molecules. Calculation of the concentration of these components would require knowledge of the pathlength through which the photons have traveled, which is not necessary for the method of the invention.

Preferably the wavelengths utilized are within the range of 700–1100 nm and most preferably 750–950 nm. However, measurements in the extended range of 600 to 1300 nm are also practicable. Absorbance measurements at each of the selected wavelengths allow for determination of the amount of Hb, $HbO_2$, cytochrome c oxidase (cytochrome $aa_3$), and correction for scattering. In brief, the steps of the method, once the absorbance measurements are taken, comprise: reference point (e.g., isosbestic point) subtraction from the signals at the other wavelengths to remove the effect of light loss due to scattering; use of in situ extinction coefficients normalized at the reference point (i.e., dividing all extinction coefficients by the extinction coefficient of hemoglobin at the reference point); and adjusting the total light absorptions for cytochrome c oxidase absorbance contributions, all of which are later discussed in more detail.

If for technical reasons a light source emitting at the isosbestic wavelength is not available, two (or more) wavelengths (preferably above and below the isosbestic point) may be substituted from which the in situ extinction coefficient at the isosbestic wavelength can then be calculated. This practice of creating an isosbestic substitute should be clearly distinguished from the use of two or more measuring wavelengths for calculating the rCBOS or the cyt c ox value.

For wavelengths in the range of 700–1100 nm, wavelength-related differences in light scattering are relatively small, especially if the range is limited to 200 nm, say from 750 to 950 nm. The existing differences in light scattering are compensated for by the use of in situ determined extinction coefficients. At these wavelengths, biologically generated fluctuations in the raw optical signals outweigh scattering differences in the near infrared region. Thus, even though there may be differences in the scattering properties of the different wavelengths used, these do not result in large errors in the determination of oxygen saturation according to the invention. Further, the later described algorithms employed in the invention use combinations with differing weighting of the same wavelengths to obtain the amounts of both $HbO_2$ and Hb (with different extinction coefficients at each wavelength) as well as of oxidized cyt c ox. Thus, any wavelength-dependent scattering is experienced in all determinations and differences are minimized.

The preferred reference wavelength is an isosbestic point, i.e. a wavelength where the two lines of the spectra for the substances to be determined intersect on a graph of absorption vs. wavelength (FIG. 1), in other words, the wavelength (s) at which the two forms of the molecule absorb equally. The preferred first (reference) wavelength is chosen to be at the isosbestic point for the two components $HbO_2$ and Hb, which is about 815 nm (between 810–820 nm). Additional wavelengths are preferably between 750–950 nm. If three wavelengths in addition to the wavelength at the isosbestic point are used, they are preferably in the ranges of 750–785, 860–875 and 895–915 nm, respectively. These wavelengths are preferably positioned at about equal absolute absorbance differences between $HbO_2$ and Hb, but also comprise the maximal absorbance of one of the forms of cytochrome c oxidase at 820 nm, approximately.

Thus, in the invention, the body part is illuminated with a number of wavelengths, at least three wavelengths, when Hb and $HbO_2$ are measured in the presence of scattering, and most preferably four wavelengths to more directly take into account the effect of the cytochrome c oxidase absorption. Data are obtained which relate to the number of molecules of each kind, which is represented by the number of molecules that have absorbed photons at the several wavelengths presented. The absorption is related to the extinction coefficient of each component at each wavelength, which was obtained from their in situ absorption spectrum. The extinction coefficients of each absorbing component are normalized to their isosbestic one.

Figure 1:
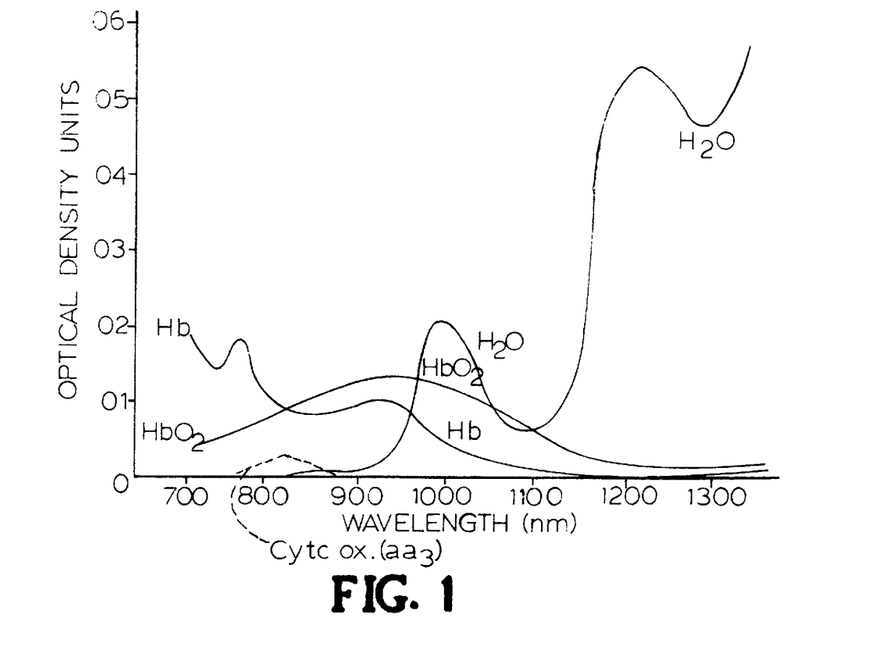
FIG. 1 is a plot of the absorption spectra of water, deoxygenated hemoglobin (Hb) and oxyhemoglobin (HbO$_2$) in solution; and of oxidized cytochrome c oxidase over the near-infrared range of about 700 to about 1300 nanometers.
Figure 2:
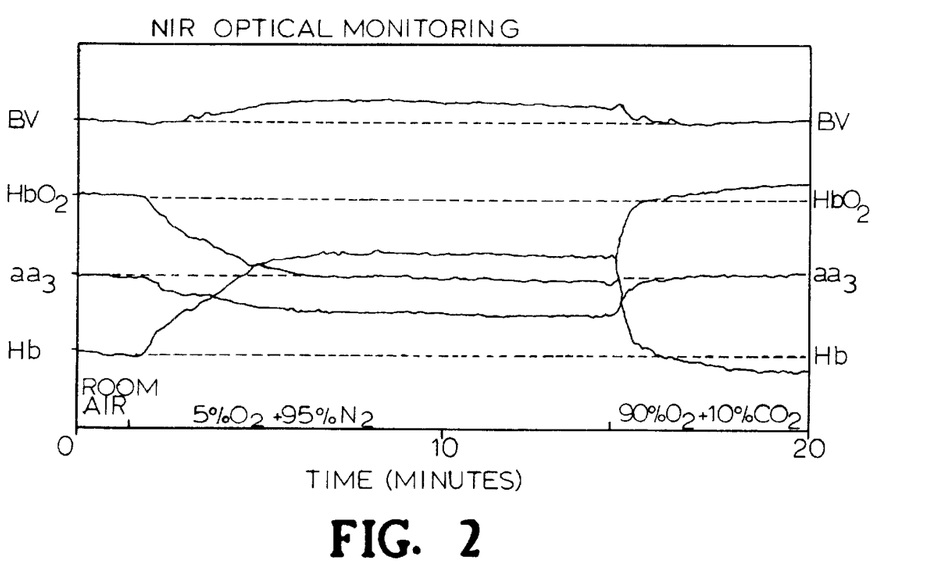
FIG. 2 is a plot illustrating traces obtained by a NIRO-SCOPE® instrument made by Vander Corporation from a rabbit's head, by transillumination, in response to ventilation successively with room air, 5% O$_2$ plus 95% N$_2$, followed by 90% O$_2$ plus 10% CO$_2$.
Figure 4:
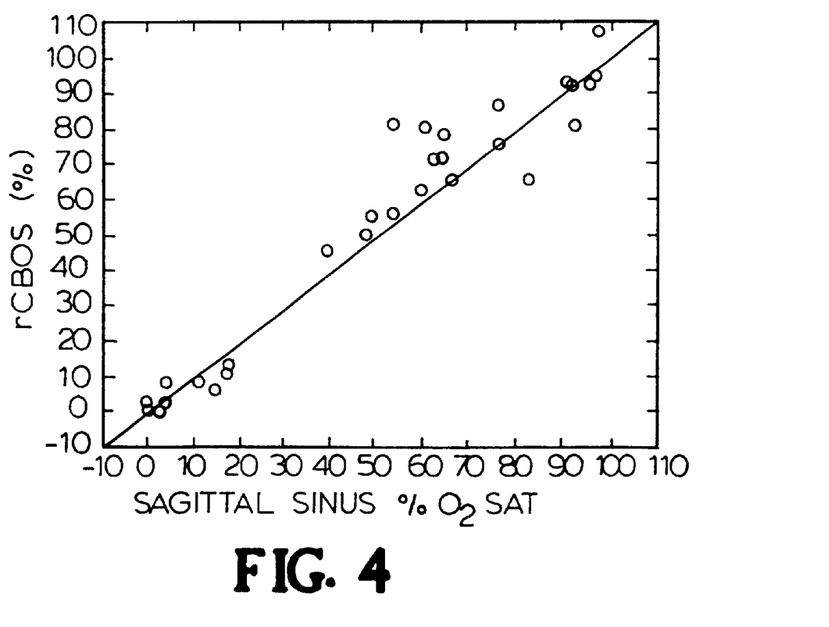
FIG. 4 is a plot illustrating the correlation of the regional Cerebral Blood Oxygen Saturation (rCBOS) determined optically and the O$_2$ Sat of blood samples drawn simultaneously from the sagittal sinus which drains the cerebral cortex.

FIGS. 1 through 3 illustrate the optical basis and the experimentally obtained biological data upon which the present invention is based. FIG. 4 compares the results obtained with the optically determined regional Cerebral Blood Oxygen Saturation (r CBOS) using the method of this invention to the values obtained by analyzing the blood draining from the cerebral cortex by sampling the sagittal sinus vein. Reference is next made to FIG. 1.

FIG. 1 depicts the NIR absorption spectra of oxygenated hemoglobin ($HbO_2$), de-oxygenated hemoglobin (Hb), water and cytochrome c oxidase (also referred to as cytochrome $aa_3$). The first three are absolute spectra, whereas the last one is the difference between the oxidized and reduced forms of the enzyme since the latter displays no identifying feature, only a gradually rising baseline from 950 to 700 nm. It should be noted that the Hb+$HbO_2$ content of the brain is quite variable depending on vascular distensions, whereas the cyt c ox content is fixed, since it is located within the brain cells. The water content within the skull and also of the cerebral tissue is amazingly constant; shifts between intra- and extracellular water do not affect total tissue water. The representation of the spectra in FIG. 1 is approximately proportioned to the normoxia condition, except that all the cerebral blood is depicted as either Hb or $HbO_2$. In reality, Hb and $HbO_2$ would contribute about 35% and 65%, respectively, to the total of all hemoglobin (the sum of Hb and $HbO_2$) in normoxia. The spectra of the three biochemical molecules, i.e. Hb, $HbO_2$ and cyt c ox, are the only ones relevant to the determination of the ratio between $HbO_2$ and ($HbO_2$+Hb). During cerebral monitoring, myoglobin does not contribute substantially to the signals, especially if the muscle mass at the temples is avoided. The invention recognizes that the cyt c ox signal can, under certain conditions, contribute a 20% error in the regional Cerebral Blood Oxygen Saturation (r CBOS) parameter and must therefor be cleansed continuously from the optical data stream.

FIG. 2 shows the data obtained from the brain of an anesthetized rabbit with the method of the invention. The responses of four relevant parameters (blood volume BV, $HbO_2$, cyt c ox also known as $aa_3$ and Hb) are caused by shifts in the nature of the constant volume ventilation gases.

FIG. 3 presents a graph of the typical behavior of cerebral cyt c ox as a function of $HbO_2$ under various ventilatory conditions of $O_2$ content, $F_1O_2$ fractional inspired $O_2$, and the effect of 5% $CO_2$. In the preferred instrument this typical curve, derived from numerous experiments, is described numerically and listed in a look-up table for subtracting the cyt c ox contributions from the raw hemoglobin+cyt c ox data. Other tissues and other investigators have shown different relations between cyt c ox reduction levels and $HbO_2$. Such data can also be described numerically and listed in the instrument's microprocessor, ready for use in different studies.

FIG. 4 correlates the optical method of the invention based on using the r CBOS with the standardly obtained percent oxygen saturation of the blood draining from the cerebral cortex into the sagittal sinus vein. The two parameter correlation coefficients for such experiments, i.e. $r^2$, are typically above 0.95. Since the venous space in the cortex far outstrips the arterial space (about 3 or 2 to 1) the r CBOS values can be used directly or corrected for 25% to 33% contribution from the arterial side. Because of the predominance of the venous blood contribution, this does not materially alter the distribution of the data points nor the $r^2$ correlation value.

FIGS. 5 and 6 depict our preferred means of entering photons into the head and recording their intensity at exit compared to their strength at entry.

An embodiment of the present invention comprises also an accounting and correction for the tissue absorbance due to cytochrome c oxidase in the equation for tissue oxygen saturation, by reiterative calculations. A reiterative process or calculation is one in which the results of a first calculation based on idealized in vivo in situ results are entered as the numerical values of the parameters to recalculate the results which are in turn used to recalculate the results, thus reducing the error in the sequential calculations to insignificance. For example, based on studies by the inventors herein, it is estimated that at the hemoglobin isosbestic point, the absorption due to cyt c ox when fully oxidized is one-eighth of the total absorption due to hemoglobin (Hb or $HbO_2$) at normoxia (normal tissue oxygenation). But at normoxia cerebral cyt c ox is 50% oxidized (FIG. 3). Using these measurements as a first step, an equation has been derived for the tissue oxygen saturation by solving simultaneous equations for the change in absorbance (A) for three or for four wavelengths with the extinction coefficients of Hb and $HbO_2$, normalized to the isosbestic one, and adjusted for the redox state of cytochrome c oxidase as if it were 50% oxidized. This is the first step and the result thereof is next corrected for the cytochrome contribution to the absorption, which in the first step was considered to be 50%, whereas for example the % $HbO_2$ was upon calculation found to be 75%, i.e. higher than in normoxia. But at such a high percentage of $HbO_2$ the cytochrome would be considerably more oxidized. Using the relationship illustrated in FIG. 3 between cytochrome and $HbO_2$, as listed in a look-up table in the instrument, the computation now arrives at the oxidized cytochrome absorption that would contribute to the total absorption at this level of $HbO_2$. Such a table consists of a tabulation of the solid line of FIG. 3 obtained from many experiments. However, after subtraction of the cytochrome contribution the calculated number of the $HbO_2$ is now underestimated because at this new lower level of $HbO_2$ the contribution by oxidized cyt $aa_3$ would not be as large. Consequently a new calculation must be made to correct for the $aa_3$ absorption at this $HbO_2$ level, etc. These reiterative calculations will produce an ever-shrinking difference between the calculated and the actual value of Hb and $HbO_2$ and thereby of the % $O_2$ Sat parameter. In the apparatus of the invention, these reiterative calculations are made in a fraction of a second by a micro-processor.

Therefore, in the method of the present invention, if the relative tissue absorptions are known at three wavelengths, one being hemoglobin's isosbestic point, one can calculate the oxygen saturation of the blood in the tissue, using reiterative correction for cyt c ox contributions.

It should be noted that the method of the present invention is not limited to data of the type shown in FIG. 3. If better data or measurements of other tissue (say muscle) reveal a different relationship, a different look-up table can be incorporated in the instrument.

Instrumentation—The Three Wavelength Method

An instrument for carrying out the method of the invention is a modification of the NIROSCOPE® instrument (Vander Corporation, Durham, N.C.). For purposes of the present invention, the NIROSCOPE® instrument is used as the control and detection system for the diode lasers, i.e. the circuitry for firing them in sequence and the means for measuring the intensity of the light emanating from the organ, i.e. the value of 1 in the Beer-Lambert relationship. Measurement of the input intensity is also used, in a unique and novel way according to the invention, for the $I_o$ parameter. Treatment and processing of the signals is also performed by the apparatus and method of the invention.

A critical component in the preferred instrumentation and method of the invention includes means for accounting for other oxygen dependent absorbing components within the tissue which alter the tissue's NIR absorbence spectra, specifically, cytochrome c oxidase. The Vander Corporation NIROSCOPE® instrument measures the change in rather than the absolute level of the cyt c ox redox state and therefore a change in the tissue absorbance due to cyt c ox. From this, the invention recognizes that the cyt c ox absorbance can be calculated as the cyt c o level, as determined by the NIROSCOPE® instrument multiplied by its relative extinction coefficient for each of the wavelengths in question. The total tissue absorbance can then be corrected for the change in absorbance due to changes in cyt $aa_3$'s redox state. This corrected tissue absorbance, now without the contribution of cyt c ox, is used in the tissue oxygen saturation equation later discussed below.

It is recognized that the variable and oxygen dependent contribution of cytochrome c oxidase to the tissue absorbance may cause an error in the tissue oxygen saturation measured by as much as 20 percent. While at most normal tissue oxygenation levels, this error will be less, probably less than ten percent, it still is necessary to account for the tissue absorbance due to cytochrome c oxidase. This is done in Examples 1 and 2 below by using estimates of cyt c ox redox levels at specific tissue oxygenation levels obtained empirically from previous studies, as done by reiterative determination discussed in Example 1.

The Two Distinct Four Wavelength Methods

Improvements in the quality of the monitored information can be achieved by two distinctly different uses of more than three wavelengths. In one case two (or more) wavelengths can be used in place of a single isosbestic wavelength if the latter is not available from the laser manufacturers. Such multiple replacement wavelengths are preferably chosen to straddle the isosbestic one.

Also recognized is a second method entailing four or more wavelengths for determining the tissue absorbance due to cyt c ox by deriving a series of simultaneous equations for HbO. Hb, and cyt c ox. As illustrated in the following Example 3, the development of three separate difference equations requires the use of at least four different wavelengths yielding three absorption differences when the isosbestic wavelength is subtracted from the other three.

The advantage of the four wavelength method is recognized in that the tissue absorbance due to cyt c ox is directly accounted for in the tissue that is currently being monitored. Also recognized is that the four wavelength method may have advantages over the reiterative determination method if the level of cytochrome c oxidase is abnormal, however it is also recognized that this benefit may be outweighed by the increased cost of the fourth laser and extra circuitry.

The features and advantages of the present invention will be more clearly understood by reference to the following examples but which are not to be construed as limiting the invention.

EXAMPLE 1

The method of the invention comprises subtracting the absorption by the body part at a common reference wavelength, for example the isosbestic point of HbO and Hb, 815 nm, from the other wavelengths used, for example 775 and 895 nm or in four wavelength instrumentation. 775, 870 and 910 nm.

The in situ extinction coefficients are obtained from the actual absorption strengths observed in the specific body part (e.g., heads) of live or recently deceased animals, such as cats, dogs, rats and pigs. These coefficients are then normalized in respect to one wavelength, most commonly at or near the isosbestic wavelength. Thus, for the wavelengths of 779 nm, 813 nm, and 895 nm in rats, the in situ relative extinction coefficients for Hb are 1.362, 1.000, and 1.025, respectively, and for HbO, they are 0.864, 1.000, and 1.395 respectively.

When utilizing these coefficients in the Isosbestic Wavelength Subtraction (IWS) equation derivation, one must account for the absorption contribution of cyt c ox in situ. From manipulation of oxygenation in animal experiments, we know that in normoxic tissue, cyt c ox is 50% oxidized and that its contribution to the absorption at 815 nm is 1/8th of the absorption contribution of Hb plus $HbO_2$. Therefore, in normoxic tissue, 50% of the total relative extinction coefficient of oxidized cytochrome c oxidase is added to the absorptions (extinction coefficients) at 779, 813, and 895 nm for Hb and $HbO_2$. This produces a new series of relative coefficients for the light absorption by the blood and cyt c ox in the tissue or organ. For example: ($eHb_{813}$=1.00, $eCyt_{813}$=0.250, $eHb_{813}$+50% $eCyt_{813}$=1.125)

The difference between the relative in situ extinction coefficients at the various wavelengths is then calculated:
1) $\Delta eHb_{779-813}$=$eHb_{779}$−$eHb_{813}$=1.427−1.125=0.302
2) $\Delta eHb_{895-813}$=$eHb_{895}$−$eHb_{813}$=1.085−1.125=−0.040
3) $\Delta eHbO_{779-813}$=$eHbO_{779}$−$eHbO_{813}$=0.929−1.125=−0.196
4) $\Delta eHbO_{895-813}$=$eHbO_{895}$−$eHbO_{813}$=1.455−1.125=0.330

Using the difference between various wavelengths, the absorption equations for Hb and HbO are derived:
5) $\Delta A_{779-813} = A_{779} - A_{813} = (\Delta eHb_{779-813} \times Hb_{am}) - (\Delta eHbO_{779-813} \times HbO_{am})$
6) $\Delta A_{895-813} = A_{895} - A_{813} = (\Delta eHb_{895-813} \times Hb_{am}) - (\Delta eHbO_{895-813} \times HbO_{am})$
in which $Hb_{am}$ and $HbO_{am}$ stand for the amounts of Hb and HbO in the tissue traversed by the photons.

When the extinction coefficients are inserted in above equations 5 and 6, the following equations are obtained:
7) $\Delta A_{779-813}$=(0.302×$Hb_{am}$)−(0.196×$HbO_{am}$)
8) $\Delta A_{895-813}$=(−0.040×$Hb_{am}$)+(0.330×$HbO_{am}$)
Solving the following simultaneous equations for Hb·d and HbO·d:
9) $Hb_{am} \times d$=(3.594×$\Delta A_{779-813}$)+(2.135×$\Delta A_{895-813}$)
10) $HbO_{am} \times d$=(0.436×$\Delta A_{779-813}$)+(3.289×$\Delta A_{895-813}$)

In the above equations 5 through 10, d is the distance across which the absorption is measured, which cancels out in the next equation for calculating the saturation percent:
11) % $O_2$ Sat=($HbO_{am}$×100)/($HbO_{am}$+$Hb_{am}$)

Therefore the percent saturation is calculated by:

$$\% O_2 Sat = \frac{(0.436 \times \Delta A_{779-813}) + (3.289 \times \Delta A_{895-813})}{(4.030 \times \Delta A_{779-813}) + (5.424 \times \Delta A_{895-813})} \times 100 \quad 12)$$

Thus, the distance factor, d, drops out in the calculation of the % $O_2$ Sat. This demonstrates the absence of a need to determine the concentrations of amounts of Hb and HbO since knowledge of the amounts suffices to calculate % $O_2$ Sat. In the case of monitoring brain oxygenation, the parameter is designated rCBOS for regional Cerebral Blood Oxygen Saturation.

When four wavelengths are used, the amounts of $HbO_2$, Hb and cytochrome c oxidase, are determined through a series of equations similar to equations 1–10.

EXAMPLE 2

Comparison of determination of oxygen saturation using the method of the invention and using the standard method with a clear solution.

The general treatment shown in Example 1 can be made more specific by the use of numbers. (For simplicity's sake the reiterative steps discussed earlier are disregarded.) In this theoretical example we use hypothetical tissue absorbances measured at wavelengths A (in the 770–790 nm range), B (800–820 nm range) and C (860–895 nm range) equal to 2.651, 2.500 and 2.480 respectively. The differences between the absorbance at the isosbestic reference wavelength B and at A and C are therefore equal to 0.151 for $\Delta A_{A-B}$ and −0.020 for $\Delta A_{C-B}$ respectively. These values are then entered, as shown below, into the % $O_2$ Sat equation (12) derived in Example 1.

$$\% O_2Sat = \frac{(0.436 \times \Delta A_{A-B}) + (3.289 \times \Delta A_{D-B})}{(4.030 \times \Delta A_{A-B}) + (5.424 \times \Delta A_{D-B})} \times 100 \quad 12)$$

$$\% O_2Sat = \frac{(0.436 \times 0.151) + (3.289 \times -0.020)}{(4.030 \times 0.151) + (5,424 \times -0.020)} \times 100$$

% $O_2$ Sat=0.01

If the $\Delta A_{A-B}$ and $\Delta A_{C-B}$ were similar to those found in highly oxygenated tissue such that $\Delta A_{A-B}$=−0.098, and $\Delta A_{C-B}$=0.168 then one could use the above saturation equation (equation 12) to find that the tissue oxygen saturation equals 100%. The intermediate $\Delta A$ values will give oxygen saturation values between 0% and 100% regardless of hemoglobin concentration.

EXAMPLE 3

The use of a fourth wavelength will allow for the direct accounting and determination of the relative amounts of cyt c ox within the monitored volume of the tissue. The use of this fourth wavelength allows for the use of three simultaneous equations that are transformed to solve for the amounts of Hb, HbO and cyt c ox separately. Therefore no reiterative correction for the oxidation level of cyt c ox needs to be made for the accurate determination of $Hb_{am}$ and $HbO_{am}$. The obtained values for $Hb_{am}$ and $HbO_{am}$ can then be used in a tissue oxygen saturation equation similar to equation 12. In the present example, we use low wavelengths, i.e. 775, 815, 872 and 895 nm. The relative extinction coefficients for Hb at these new wavelengths (A, B, C, and D) are 1.362, 1.000, 0.998, and 1.025 respectively; the relative extinction coefficients for HbO at the above wavelengths are 0.864, 1.000, 1.360, and 1.395 respectively; and the relative extinction coefficients for Cyt c ox at these wavelengths are 0.140, 0.250, 0.226, 0.120 respectively.
13) $\Delta eHb_{A-B}$=1.320−1.000=0.320
14) $\Delta eHb_{C-B}$=1.000−1.000=0.0
15) $\Delta eHb_{D-B}$=1.030−1.000=0.030
16) $\Delta eHb_{A-B}$=0.884−1.000=0.116
17) $\Delta eHbO_{C-B}$=1.360−1.000=0.360
18) $\Delta eHbO_{D-B}$=1.408−1.000=0.408
19) $\Delta eCyt_{A-B}$=0.140−0.250=−0.110
20) $\Delta eCyt_{C-B}$=0.226−0.250=−0.024
21) $\Delta eCyt_{D-B}$=0.102−0.250=−0.148
The above extinction coefficient differences are now placed into the $\Delta A$ equations:
22) $\Delta A_{A-B} = (\Delta eHb_{A-B} \times Hb_{am}) + (\Delta eHbO_{A-B} \times HbO_{am}) + (\Delta eCyt_{A-B} \times Cyt_{am})$
23) $\Delta A_{C-B} = (\Delta eHb_{C-B} \times Hb_{am}) + (\Delta eHbO_{C-B} \times HbO_{am}) + (\Delta eCyt_{C-B} \times Cyt_{am})$
24) $\Delta A_{D-B} = (\Delta eHb_{D-B} \times Hb_{am}) + (\Delta eHbO_{D-B} \times HbO_{am}) + (\Delta eCyt_{D-B} \times Cyt_{am})$
25) $\Delta A_{A-B}$=0.320×$Hb_{am}$−0.116×$HbO_{am}$−0.110×$Cyt_{am}$
26) $\Delta A_{C-B}$=0.0×$Hb_{am}$+0.360×$HbO_{am}$−0.024×$Cyt_{am}$
27) $\Delta A_{D-B}$=0.030×$Hb_{am}$+0.408×$HbO_{am}$−0.148×$Cyt_{am}$
28) $Hb_{am}$=3.439×$\Delta A_{A-B}$+4.907×$\Delta A_{C-B}$−3.352×$\Delta A_{D-B}$
29) $HbO_{am}$=0.057×$\Delta A_{A-B}$+3.484×$\Delta A_{C-B}$−0.607×$\Delta A_{D-B}$
30) $Cyt_{am}$=0.854×$\Delta A_{A-B}$+10.60×$\Delta A_{C-B}$−9.111×$\Delta A_{D-B}$
The equations for $Hb_{am}$ and $HbO_{am}$ may now be implemented into the standard % $O_2$ Saturation equation (equation #11) with the following results:

$$\% O_2Sat = \frac{0.057 \times \Delta A_{A-B} + 3.484 \times \Delta A_{C-B} - 0.607 \times \Delta A_{D-B}}{3,496 \times \Delta A_{A-B} + 8.391 \times \Delta A_{C-B} - 3.959 \times \Delta A_{D-B}} \quad 31)$$

The effects due to the absorption of light by Cyt c ox have been removed, or minimized by accounting for the amount of Cty c ox in the tissue volume. Therefore the equation 31 may be used without resorting to the reiterative calculation of % $O_2$ Sat and the contribution of Cyt c ox to the tissue absorbance.

SUMMARY

In summary, the invention permits oxygen saturation of the blood to be determined without having to determine the optical path length through the tissue. Further, the invention does not require measuring the concentrations of the components Hb and $HbO_2$. The fact that the light at multiple wavelengths is entered in the body through one aperture, either sequentially or simultaneously after mixing, also insures that the tissue being measured is exposed to light of the same kind. That is, all of the wavelengths strike the tissue at the same point. This prevents for example, the possibility of entering one wavelength in an arterial area and another in a venous one.

Also to be noted is that, even though the relative absorption strength at specific wavelengths is unpredictably distorted by the described scattering effects, the apparatus and method of the invention mitigates these effects by using the in vivo, in situ absorption spectra generated directly from the organ being monitored or closely similar ones. The invention recognizes that the signal is generated by a combination of the arterial, venous and capillary fractions of the blood within the monitored tissue and is therefore more representative of the status of that tissue than the commonly used pulse oximeter signal which indicates only the oxygen saturation of arterial blood.

The novel method described herein, emphasizes the subtraction of high losses at the isosbestic point of $Hb/HbO_2$ from absorptions at other wavelengths. The resulting absorption difference data are then treated according to the in situ absorption spectra in the form of two simultaneous equations if the three wavelengths instrumentation is used. In any case, however, cyt c ox absorption is accounted for and eliminated.

Application of the three wavelength method requires the indirect reiterative elimination of cyt c ox contributions to the overall absorption. The situation in the case of four (or more) measuring wavelengths is somewhat simplified. The same process of subtracting the light loss at the isosbestic wavelength yields three (or more) simultaneous equations. This suffices to solve directly for three unknowns; and for four or more in the same manner as described for the three wavelength technique. Thus, in the four wavelength case, cytochrome c oxidase can be determined directly and reiterative accounting of optical interactions is not required.

The applicants have discovered the importance of eliminating fiber optics and using mixing devices with a single aperture to homogenize and enter the light into the organ to be monitored. Aside from the fiber-optic fibers being fragile, their use leads to severe light losses and greatly complicates the eventual replacement of a defective laser. In a preferred embodiment, less powerful (and therefor less expensive and less vulnerable) lasers are mounted directly on the device that mixes the light of various wavelengths. As previously mentioned, the use of a single aperture to enter the mixed light into the organ eliminates the possibility of entering light of one wavelength into a venous area and light of another wavelength directly at an artery in the tissue. In addition, the invention requires the identification by the detection system of the individual wavelength signals. In preferred embodiments, this can be achieved by alternately activating each laser in a specified sequence or by modulating the output of the various lasers at different frequencies followed by demodulation in the electronic detector circuitry.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A non-invasive, in-vivo, in-situ spectrophotometric method of determining percent oxygen saturation of hemoglobin in blood within a part of a body exhibiting active oxidative metabolism without having to consider changes in optical path length, concentrations of $HbO_2$ and Hb or degree of light scattering which takes place during such determination, comprising:

(a) selecting electromagnetic radiation of at least three wavelengths to establish at least three selected wavelengths and wherein said at least three selected wavelengths includes a first wavelength which is a reference wavelength, a second wavelength which is a measuring wavelength and a third wavelength which is a measuring wavelength;

(b) irradiating a selected location on said body part with light which at said location includes each of said selected wavelengths each of measured intensity;

(c) measuring the light intensity and calculating the absorbance of each of said selected wavelengths after passing through said body part;

(d) determining the differences between the absorption of light of said reference wavelength and said second and said third wavelengths by subtraction of the absorbance of said reference wavelength from that of said second and third wavelengths;

(e) entering said differences of absorptions of the light of said reference wavelength and said second and third wavelengths in first and second equations derived from differences between relative in-situ determined isosbestic normalized extinction coefficients of Hb and $HbO_2$ at said reference wavelength and said second and third wavelengths and solving said first and second equations for the amounts of $HbO_2$ and Hb encountered as distinct from calculated concentrations;

(f) continuously correcting said amounts for absorption contributions of cytochrome c oxidase to said percent oxygen saturation; and (g) determining tissue oxygen saturation percent as a ratio of the amount of $HbO_2$ to the total amount of hemoglobin ($HbO_2$+Hb) times 100.

2. The method of claim 1 wherein said at least three selected wavelengths are selected to be in the region between 600 and 1300 nm.

3. The method of claim 2, wherein the said reference wavelength is at an isosbestic point for oxygenated hemoglobin and deoxygenated hemoglobin of approximately 815 nm.

4. The method of claim 1, further comprising a fourth wavelength in the range of 860–875 nm.

5. The method of claim 1, wherein said step of continuously correcting said amounts is based on determining and entering the extinction coefficient for cytochrome c oxidase into said equations.

6. The method of claim 5, wherein the correction for absorbance contribution of cytochrome c oxidase is performed in a reiterative manner to provide a close approximation of the correction to be applied for determination of tissue oxygen saturation existing during conditions away from normoxia.

7. The method of claim 1, wherein the percent of oxygen saturation of the hemoglobin in the blood is continuously corrected for changes in cytochrome c oxidase by determining the trend of absorbance of cytochrome c oxidase.

8. The method of claim 1, wherein the reference wavelength is at an isosbestic point for oxygenated hemoglobin and deoxygenated hemoglobin of approximately 815 nm.

9. The method of claim 1, wherein said reference wavelength is in the range of 810–820 nm, said first measuring wavelength is in the range of 750–785 nm, and said second measuring wavelength is in the range of 895–925 nm.

10. The method of claim 1 wherein said at least three selected wavelengths comprises four wavelengths and includes first and second reference wavelengths on opposite sides of an isosbestic point of said hemoglobin.

11. A non-invasive, in-vivo, in-situ spectrophotometric method of determining the percent oxygen saturation of the hemoglobin in the blood within a part of the body exhibiting active oxidative metabolism without having to consider changes in the optical path length, concentrations of $HbO_2$ and Hb or degree of light scattering which takes place during such determination, comprising:

(a) selecting electromagnetic radiation of at least three wavelengths to establish at least three selected wavelengths and wherein said at least three selected wavelengths includes a first wavelength which is a reference wavelength, a second wavelength which is a measuring wavelength and a third wavelength which is a measuring wavelength;

(b) irradiating a selected location on said body part with light which at said location includes each of said selected wavelengths each of measured intensity;

(c) measuring the light intensity and calculating the absorbance of each of said selected wavelengths after passing through said body part;

(d) determining the differences between the absorption of light of said reference wavelength and said second and said third wavelengths by subtraction of the absorbance of said reference wavelength from that of said second and third wavelengths;

(e) entering said differences of absorptions of the light of said reference wavelength and said second and third wavelengths, in first and second equations derived from differences between relative in-situ determined isosbestic normalized extinction coefficients of Hb and $HbO_2$ at said reference wavelength and said second and third wavelengths and solving said first and second equations for the amounts of $HbO_2$ and Hb encountered as distinct from calculated concentrations;

(f) continuously correcting said amounts for absorption contributions of cytochrome c oxidase to said percent oxygen saturation based on determining and entering the extinction coefficient for cytochrome c oxidase into said equations and performing said correction in a reiterative manner to provide a close approximation of the correction to be applied for determination of tissue oxygen saturation existing during conditions away from normoxia; and (g) determining tissue oxygen saturation percent as a ratio of the amount of $HbO_2$ to the total amount of hemoglobin ($HbO_2$+Hb) times 100.

12. A non-invasive, in-vivo, in-situ spectrophotometric method of determining the percent oxygen saturation of the hemoglobin in the blood within a part of the body exhibiting active oxidative metabolism without having to consider changes in the optical path length, concentrations of $HbO_2$ and Hb or degree of light scattering which takes place during such determination, comprising:

(a) selecting electromagnetic radiation of at least three wavelengths to establish at least three selected wavelengths and wherein said at least three selected wavelengths includes a first wavelength which is a reference wavelength, a second wavelength which is a measuring wavelength and a third wavelength which is a measuring wavelength;

(b) irradiating a selected location on said body part with light which at said location includes each of said selected wavelengths each of measured intensity;

(c) measuring the light intensity and calculating the absorbance of each of said selected wavelengths after passing through said body part;

(d) determining the differences between the absorption of light of said reference wavelength and said second and said third wavelengths by subtraction of the absorbance of said reference wavelength from that of said second and third wavelengths;

(e) entering said differences of absorptions of the light of said reference wavelength and said second and third wavelength, in first and second equations derived from differences between relative in-situ determined isosbestic normalized extinction coefficients of Hb and $HbO_2$ at said reference wavelength and said second and third wavelengths and solving said first and second equations for the amounts of $HbO_2$ and Hb encountered as distinct from calculated concentrations;

(f) continuously correcting said amounts for absorption contributions of cytochrome c oxidase to said percent oxygen saturation;

(g) continuously correcting the percent of oxygen saturation of the hemoglobin in the blood for changes in cytochrome c oxidase by determining the trend of absorbance of cytochrome c oxidase; and (h) determining tissue oxygen saturation percent as a ratio of the amount of $HbO_2$ to the total amount of hemoglobin ($HbO_2$+Hb) times 100.

13. A non-invasive, in-vivo, in-situ spectrophotometric method for calculating oxygen saturation of the hemoglobin in the blood in tissue of a body organ exhibiting active oxidative metabolism without having to consider changes in the optical path length, concentrations of $HbO_2$ and Hb or scattering which takes place during such determination, comprising:

(a) establishing a source of multiple and at least three wavelengths of light and at least one of which is substantially at an isosbestic point of oxy- and deoxyhemoglobin;

(b) contacting a selected location on said organ with said light to cause said light to be selectively either reflected from or passed through said organ and when passed through said organ being of sufficient intensity to pass both through said organ as well as through any skin and bone in the path of said light;

(c) prior to contacting said organ with said light, mixing said multiple wavelengths of light such that said tissue at said location receives light of each of said wavelengths homogenously;

(d) creating signals representative of the absorption by the tissue for each of the wavelengths;

(e) processing said signals by subtracting the absorbance by the tissue for the wavelength at said isosbestic point from the absorbance of each of the other wavelengths to establish for each other wavelength a difference between such absorbances;

(f) processing signals representative of said differences and determining from the differences the oxygen saturation of the hemoglobin in the blood in the tissue; and (g) during said processing continuously correcting said amounts for absorption contributions of cytochrome c oxidase to said percent oxygen saturation in a reiterative manner.

14. A non-invasive, in-vivo, in-situ spectrophotometric apparatus for calculating oxygen saturation in the hemoglobin in blood in tissue of a body organ exhibiting active oxidative metabolism independent of changes in optical path length, concentration of $HbO_2$ and Hb and scattering, comprising:

(a) a plurality of light sources located externally of the organ and providing multiple and at least three wavelengths of light and at least one of which is at an isosbestic point of hemoglobin;

(b) means for mixing said wavelengths of light to provide a beam of light containing each of said wavelengths;

(c) means for receiving said beam of light and contacting said organ with said light to cause said light to be selectively either reflected from or passed through said organ and when passed through said organ being of sufficient intensity to pass both through said organ as well as through any skin and bone in the path of said light;

(d) means for comparing the absorbance by the tissue for each of the said three wavelengths after being passed through the organ and creating signals representative of such absorbance;

(e) means for processing said signals by subtracting the absorbance by the tissue for the wavelength at said isosbestic point from the absorbance of each of the other wavelengths to establish for each other wavelength a difference between such absorbances;

(f) means for continuously correcting said processing by reiterative calculation for the relative tissue absorptions associated with said wavelengths for the absorption contribution of cytochrome c oxidase; and (g) means for processing signals representative of said differences and determining from the differences the oxygen saturation of the blood in the tissue.

15. A non-invasive, in-vivo, in-situ spectrophotometric method of determining the percent of oxygen saturation of the hemoglobin in the blood within a part of the body exhibiting active oxidative metabolism without having to consider changes in the optical path length, concentrations of $HbO_2$ and Hb or scattering which takes place during such determination, comprising:

(a) selecting electromagnetic radiation of three wavelengths, one of said wavelengths being at an isosbestic point of hemoglobin;

(b) irradiating a selected location on the tissue comprising said body part with light which at said location includes light of each of said selected wavelengths;

(c) determining the relative absorptions of each of said wavelengths by said body part tissue;

(d) adjusting by reiterative calculation the relative tissue absorptions associated with said wavelengths for contributions to said absorptions by cytochrome c oxidase;

(e) processing signals representative of said absorptions and adjustment; and (f) utilizing said processing to calculate the percent oxygen saturation of the hemoglobin in the blood within said body part.

16. A non-invasive, in-vivo, in-situ spectrophotometric method of determining the percent of oxygen saturation of the hemoglobin in the blood within a part of the body exhibiting active oxidative metabolism without having to consider changes in the optical path length, concentrations of $HbO_2$ and Hb or scattering which takes place during such determination, comprising:

(a) selecting electromagnetic radiation of three wavelengths, one of said wavelengths being at an isosbestic point of hemoglobin;

(b) irradiating a selected location on the tissue comprising said body part with light which at said location includes light of each of said selected wavelengths;

(c) determining the relative absorptions of each of said wavelengths by said body part tissue;

(d) adjusting by reiterative calculation the relative tissue absorptions associated with said wavelengths for contributions to said absorptions by cytochrome c oxidase;

(e) processing signals representative of said absorptions and adjustment; and (f) utilizing said processing to calculate the percent oxygen saturation of the hemoglobin in the blood within said body part.

* * * * *